United States Patent
Cheng et al.

(10) Patent No.: US 10,740,931 B2
(45) Date of Patent: Aug. 11, 2020

(54) METHOD FOR PERFORMING MAGNETIC RESONANCE IMAGING RECONSTRUCTION WITH UNSUPERVISED DEEP LEARNING

(71) Applicant: The Board of Trustees of the Leland Stanford Junior University, Palo Alto, CA (US)

(72) Inventors: Joseph Y. Cheng, Los Altos, CA (US); Feiyu Chen, Stanford, CA (US); John M. Pauly, Stanford, CA (US); Shreyas S. Vasanawala, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 156 days.

(21) Appl. No.: 16/147,830

(22) Filed: Sep. 30, 2018

(65) Prior Publication Data

US 2020/0105031 A1   Apr. 2, 2020

(51) Int. Cl.
| | | |
|---|---|---|
| *G06K 9/00* | (2006.01) | |
| *G06T 11/00* | (2006.01) | |
| *G06N 3/08* | (2006.01) | |
| *G16H 30/40* | (2018.01) | |
| *G06N 3/04* | (2006.01) | |

(52) U.S. Cl.
CPC .............. *G06T 11/005* (2013.01); *G06N 3/04* (2013.01); *G06N 3/088* (2013.01); *G16H 30/40* (2018.01); *G06T 2210/41* (2013.01)

(58) Field of Classification Search
None
See application file for complete search history.

(56) References Cited

U.S. PATENT DOCUMENTS

| | | | |
|---|---|---|---|
| 7,688,068 B2 | 3/2010 | Beatty | |
| 8,717,024 B2 | 5/2014 | King | |
| 8,948,536 B2 | 2/2015 | Boernert | |
| 2019/0325621 A1* | 10/2019 | Wang | ............ A61B 6/037 |

OTHER PUBLICATIONS

Lustig M, et al. Sparse MRI: The application of compressed sensing for rapid MR imaging. Magnetic resonance in medicine. 2007, 58(6):1182-1195.
Hammernik, K. et al. Learning a Variational Network for Reconstruction of Accelerated MRI Data. arXiv: 1704.00447 [cs.CV] (2017).
Diamond, S., Sitzmann, V., Heide, F. & Wetzstein, G. Unrolled Optimization with Deep Priors. arXiv: 1705.08041 [cs.CV] (2017).
Beck A, Teboulle M. A fast iterative shrinkage-thresholding algorithm for linear inverse problems. SIAM journal on imaging sciences. Mar. 4, 2009;2(1):183-202.

* cited by examiner

*Primary Examiner* — Atiba O Fitzpatrick
(74) *Attorney, Agent, or Firm* — Lumen Patent Firm

(57) ABSTRACT

A method for magnetic resonance imaging performs unsupervised training of a deep neural network of an MRI apparatus using a training set of under-sampled MRI scans, where each scan comprises slices of under-sampled, unclassified k-space MRI measurements. The MRI apparatus performs an under-sampled scan to produce under-sampled k-space data, updates the deep neural network with the under-sampled scan, and processes the under-sampled k-space data by the updated deep neural network of the MRI apparatus to reconstruct a final MRI image.

6 Claims, 4 Drawing Sheets

METHOD FOR PERFORMING MAGNETIC RESONANCE IMAGING RECONSTRUCTION WITH UNSUPERVISED DEEP LEARNING

STATEMENT REGARDING FEDERALLY SPONSORED RESEARCH OR DEVELOPMENT

This invention was made with Government support under contract R01 EB019241 awarded by the National Institutes of Health, and under contract R01 EB009690 awarded by the National Institutes of Health. The Government has certain rights in the invention.

FIELD OF THE INVENTION

The present invention relates generally to magnetic resonance imaging. More specifically, it relates to techniques for reconstruction MRI images using a deep neural networks.

BACKGROUND OF THE INVENTION

Magnetic resonance imaging (MRI) can provide high-resolution structural and functional images with excellent soft-tissue contrast. It is widely used in diagnoses and treatments of various diseases. Accelerating MRI by under-sampling in the spatial-frequency domain (k-space) is commonly used to reduce motion-related artifacts and improve scan efficiency. Parallel imaging and compressed sensing (PICS) has been widely used to reconstruct under-sampled MR scans. However, these techniques may be computationally expensive for high spatial/temporal resolution acquisitions, resulting in significant delays in patient care.

Recently, supervised deep learning approaches have been applied to MRI reconstruction, and these approaches have been demonstrated to significantly improve the speed of reconstruction by parallelizing the computation and using a pre-trained neural network model. In these methods, it is necessary to collect sufficient ground-truth images to train the neural network. However, for many applications, ground-truth images are not available or extremely difficult to acquire. For example, in dynamic contrast-enhanced MR scans, image contrast is changing very rapidly after the injection of the contrast agent, which makes it impossible to acquire a fully-sampled k-space for a certain image contrast. In addition, for some applications, even when fully-sampled scans are achievable, it is clinically impractical to collect hundreds of these raw datasets, as each of them may take hours to acquire without PICS-based under-sampling.

BRIEF SUMMARY OF THE INVENTION

The present invention provides techniques that enable deep-learning reconstruction of MRI images when fully-sampled reference images are not available. The technique uses unsupervised deep-learning to train a deep neural network for MR reconstruction without the use of ground truth images. Because the technique does not rely on any ground truth reference images to train the network, the applications for deep learning reconstruction are increased. In addition, the training set for unsupervised learning does not require fully-sampled data. The network is trained with under-sampled data. The network model can also be updated with under-sampled data.

This unsupervised deep-learning technique for MRI reconstruction by training a deep neural network can use a loss function that enforces both data consistency and additional image features, such as image sharpness and spatial-temporal low rank. Compared to conventional methods, this technique can train a deep neural network without the use of ground truth reference images, which enables deep learning reconstruction for applications in which ground truth images are difficult or impossible to acquire. The trained network can significantly improve reconstruction speed without degrading the image quality. In addition, the technique has several other advantages, including the following: fast image reconstruction with nearly instant image feedback in clinical scans; flexibility in loss functions, regularization terms, and data-consistency blocks; allows use of a windowing function, which can be used to perform soft-gated motion correction; allows updating of the model in real time, which improves the robustness of deep-learning reconstruction as the number of scans increases.

In one aspect, the invention provides a method for magnetic resonance imaging comprising performing unsupervised training of a deep neural network of an MRI apparatus using a training set of under-sampled MRI scans, wherein each scan comprises slices of under-sampled, unclassified k-space MM measurements; performing by the MRI apparatus an under-sampled scan to produce under-sampled k-space data; updating the deep neural network with the under-sampled scan; and processing the under-sampled k-space data by the updated deep neural network of the MRI apparatus to reconstruct a final MRI image.

The unsupervised training of the deep neural network of the MRI apparatus using the training set of under-sampled MRI scans comprises selecting a set of training batches, where each of the training batches is a set of under-sampled slices randomly selected from the training set of under-sampled MRI scans; and updating with backpropagation the deep neural network with the training batches by sequentially applying to the deep neural network the training batches, evaluating for each applied training batch an unsupervised loss function.

The unsupervised loss function is preferably a sum over slices in the applied training batch of a regularization term plus a difference between a slice in the applied training batch and an encoding operator applied to an image output from the deep neural network from applying the slice in the applied training batch. The regularization term is preferably a sum over products of constant regularization coefficients and regularization functions of the image output from the deep neural network.

The deep neural network preferably comprises a set of neural network channels for processing in parallel the slices in the applied training batch, where each of the channels produces the image output from the deep neural network from applying the slice in the applied training batch, where each channel comprises a sequence of block pairs, where each of the block pairs comprises a data consistency block and a neural network block. The data consistency block processes the slice of the applied training batch and a prior intermediate image from a prior block pair to produce an output, and the neural network block processes the output to produce an intermediate image for a subsequent block pair, where the neural network block preferably comprises a channel augmentation layer, multiple convolution layers, and a channel combination layer.

Preferably, the training set of under-sampled MRI scans comprises scans of more than 100 different subjects, and each scan comprises at least 10 slices of under-sampled, unclassified k-space MRI measurements.

DETAILED DESCRIPTION OF THE INVENTION

Figure 1A:
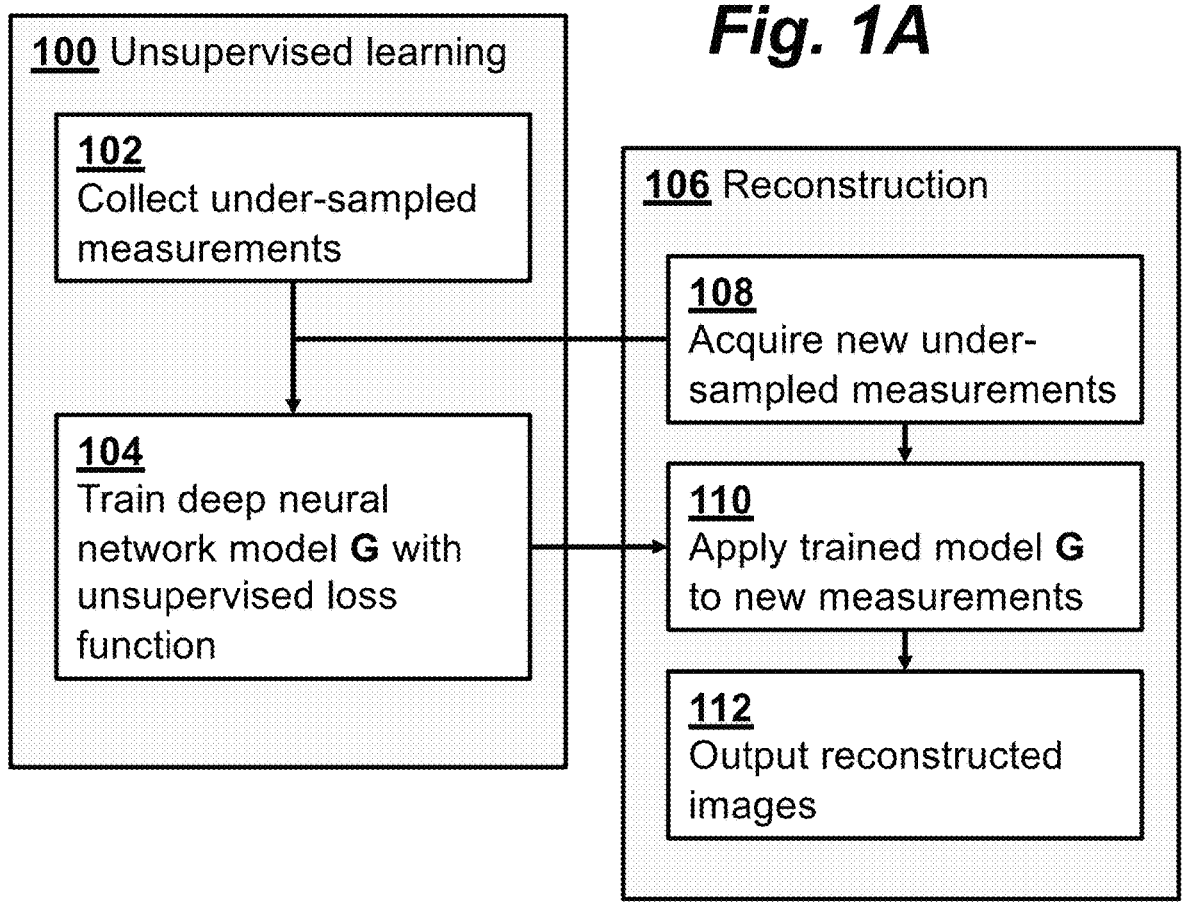
FIG. 1A is a flow chart illustrating an overview of the method of MRI imaging according to an embodiment of the present invention.

An overview of a workflow according to an embodiment of the invention is shown in FIG. 1A. There are two major steps: unsupervised training 100 and reconstruction 106. The training step 100 performs unsupervised learning based on under-sampled data acquired from a variety of different scans. The reconstruction step 106 uses the trained model to perform inference and reconstruct and image from a clinical under-sampled scan. The model can be updated by training with the new under-sampled data. The data is then applied to the model to produce a reconstructed output image.

The unsupervised training 100 of the network is typically performed by the manufacturer of the MRI apparatus, but the same training technique is used in the clinical setting for updating the model during clinical use, as will be described later. In the initial training, existing under-sampled scans are collected in step 102 based on under-sampled data acquired from a variety of different scans. In step 104 this under-sampled data is used as training data to perform unsupervised training of a pre-designed network architecture by minimizing a loss function using backpropagation. The loss function only depends on the under-sampled measurement data and the image output from the network. Therefore, the training process requires no ground truth images. The details of the network architecture and the proposed loss function are explained in more detail below. In the training, batches of the under-sampled measurements in k-space pass through sequences of data-consistency blocks and neural network blocks. Parameters in both the data-consistency blocks and the neural network blocks are trained by minimizing the loss function. After training is done, outputs of the last neural network block are used as the final reconstruction.

The reconstruction of images from scans in step 106 is typically performed by the end user of the MRI apparatus in a clinical setting, but may also be performed by the manufacturer during testing and calibration. In step 108 a new under-sampled scan is performed to produce under-sampled data. The slices from this data are randomly selected to create batches that are applied as input to update the trained model, using the same training technique 104 used for the initial training. Updating the model is important in cases where data from a scan is substantially different from the data previously used to train the model. Updating the model will then provide improved image quality at the cost of additional computational complexity and time. In step 110, the batches of slices generated from the new scan data are then applied to the updated model to reconstruct an image of the new scan, which is then output in step 112.

Figure 2:
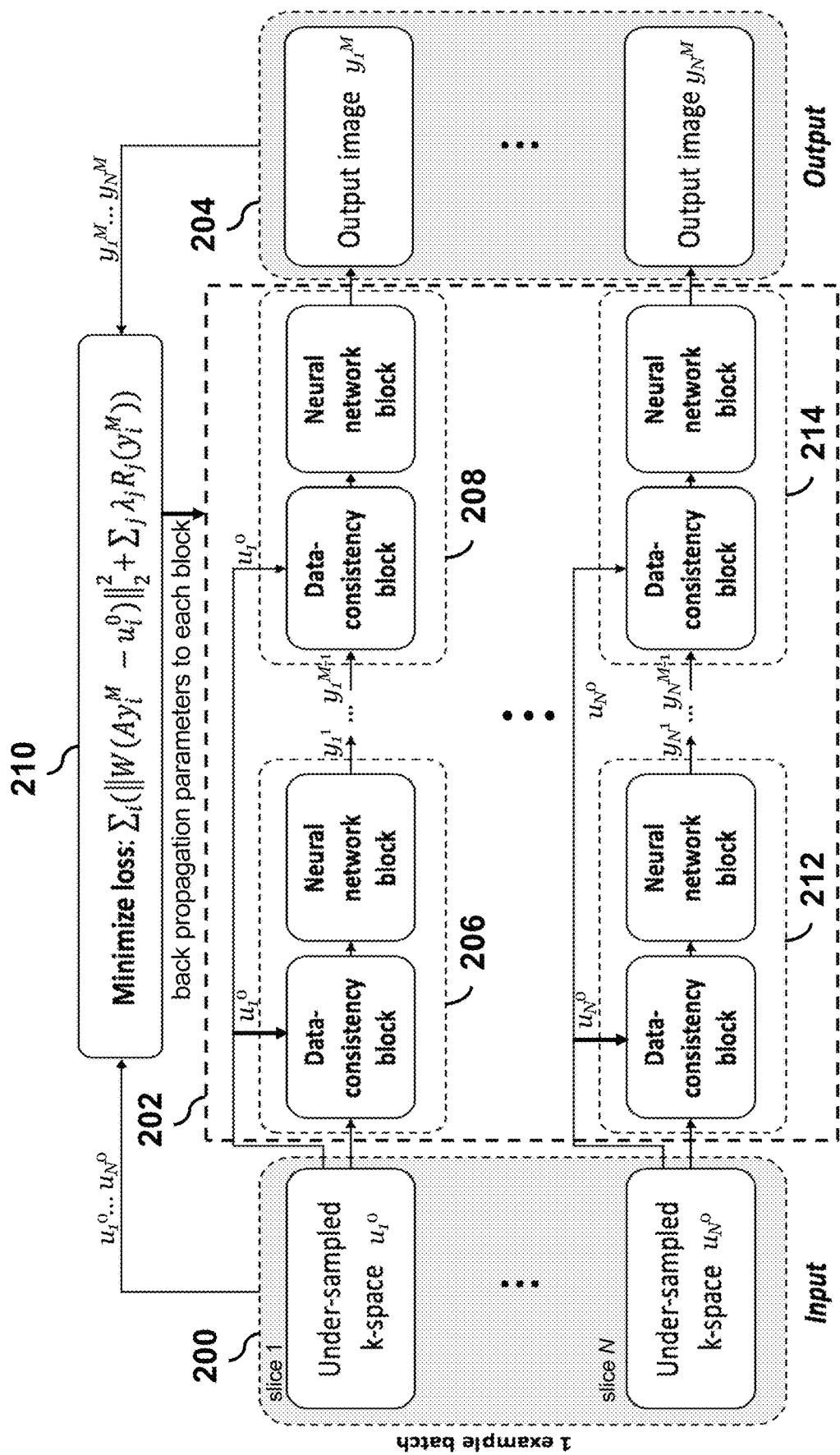
FIG. 2 is a schematic block diagram illustrating the training pipeline of an unsupervised deep-learning technique according to an embodiment of the present invention.

Details of the training and reconstruction pipeline are shown in FIG. 2. The training involves applying slices of k-space data 200 to the network 202 to produce output image data 204. Minimizing a loss function 210 produces back propagation parameters to update neural network blocks in the network 202. The purpose of training is to build a model with trained parameters for fast reconstruction.

Figure 1B:
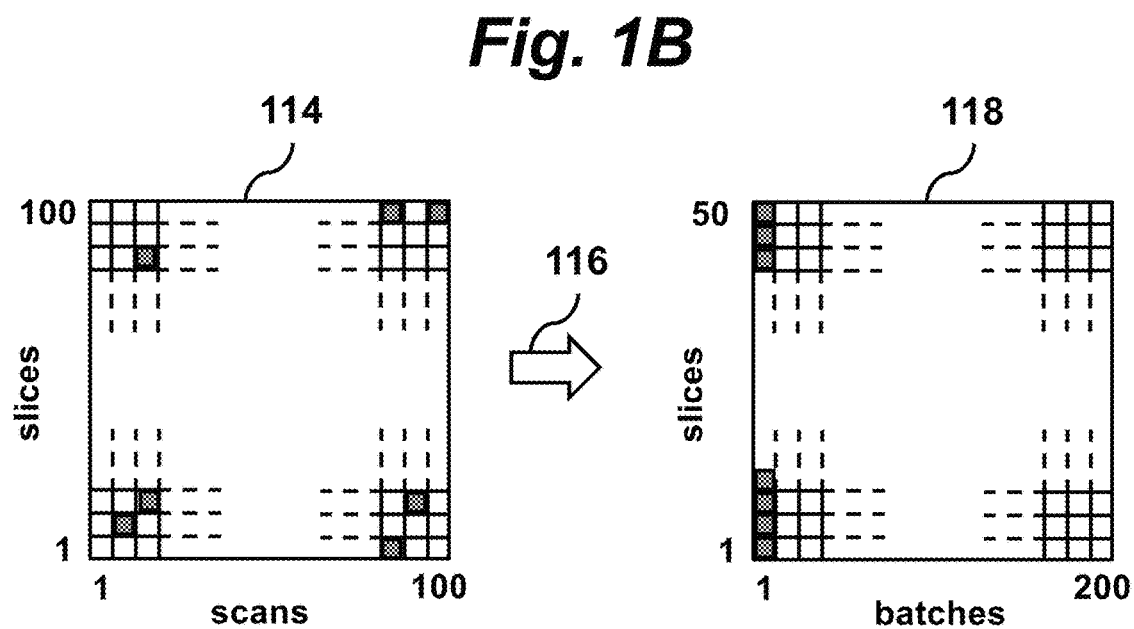
FIG. 1B is a diagram illustrating random sampling of under-sampled slices from an image training set to produce batches of slices, according an embodiment of the present invention.

The training uses a set of preferably 100 or more scans that are collected using routine scan protocols with acceleration, preferably using different sampling patterns. In each scan, multiple slices (typically 10-200 in number) are acquired. Each slice is an under-sampled k-space measurement. The training set may be visualized as a grid 114, as shown in FIG. 1B. The training set is then used to generate batches of slices for application to the network, forming a training set of batches 118. Each batch contains a random sampling of under-sampled slices from the training set 114. The slices in a given batch are randomly chosen from existing scans, possibly from different scans. All batches have the same number of slices, typically between 10-100 slices in each batch. FIG. 1B shows an example with 100 scans having 100 slices each, and 200 batches of 50 slices each.

Returning to FIG. 2, these batches are input sequentially in time into the network. The figure shows a batch 200 of N slices, denoted $u_1^O, \ldots, u_N^O$, passing through N corresponding processing channels of the network 202 to produce N corresponding output images 204, denoted $y_1^M, \ldots, y_N^M$. Each of the N channels contains a chain of M block pairs. For example, the first chain contains pair 206 through 208, and the last chain contains pairs 212 through 214. Each block pair contains a data-consistency block and neural-network block, as will be described in more detail later in relation to FIG. 3. In one embodiment, each chain has 10 block pairs for single-phase reconstruction. In another embodiment, each chain has 4 block pairs for multi-phase reconstruction. The k-space data $u_i^O$ for slice i in the batch 200 is fed as input to each of the block pairs in processing chain i of the network 202. The output of the m-th block pair in the chain i is an image $y_i^m$, which is fed as input to the next block pair in the chain, so that chain of images $y_i^O, \ldots, y_i^M$ are generated as the data passes through the block pairs of the chain i, ultimately producing output image $y_i^M$ at the end of the chain. Thus, the N chains process the N slices $u_1^O, \ldots, u_N^O$, in parallel through the N chains of the network to produce the N output images $y_1^M, \ldots, y_N^M$.

Parameters in both data-consistency blocks and neural-network blocks are optimized by minimizing a loss function 210 using backpropagation based on raw measurements $u_1^O, \ldots, u_N^O$, and the final output of the network $y_1^M \ldots, y_N^M$. After the minimization is done, the trained model of network 202 is saved for future reconstruction.

For a clinical scan, the reconstruction pipeline begins by loading the trained model (a network with optimized parameters for each operation) that was saved after completion of the training described above. An MRI scan is then performed, producing a new under-sampled k-space dataset, which is input as batches of randomly selected slices into the trained model to update it, using the same techniques described above for training. The under-sampled k-space dataset is then applied to the updated model to obtain output reconstructed images. Optionally, the reconstructed data is passed through additional standard steps in an imaging pipeline that may include filtering, gradient non-linearity correction, Fourier transform, and/or sum-of-squares operation.

Figure 3:
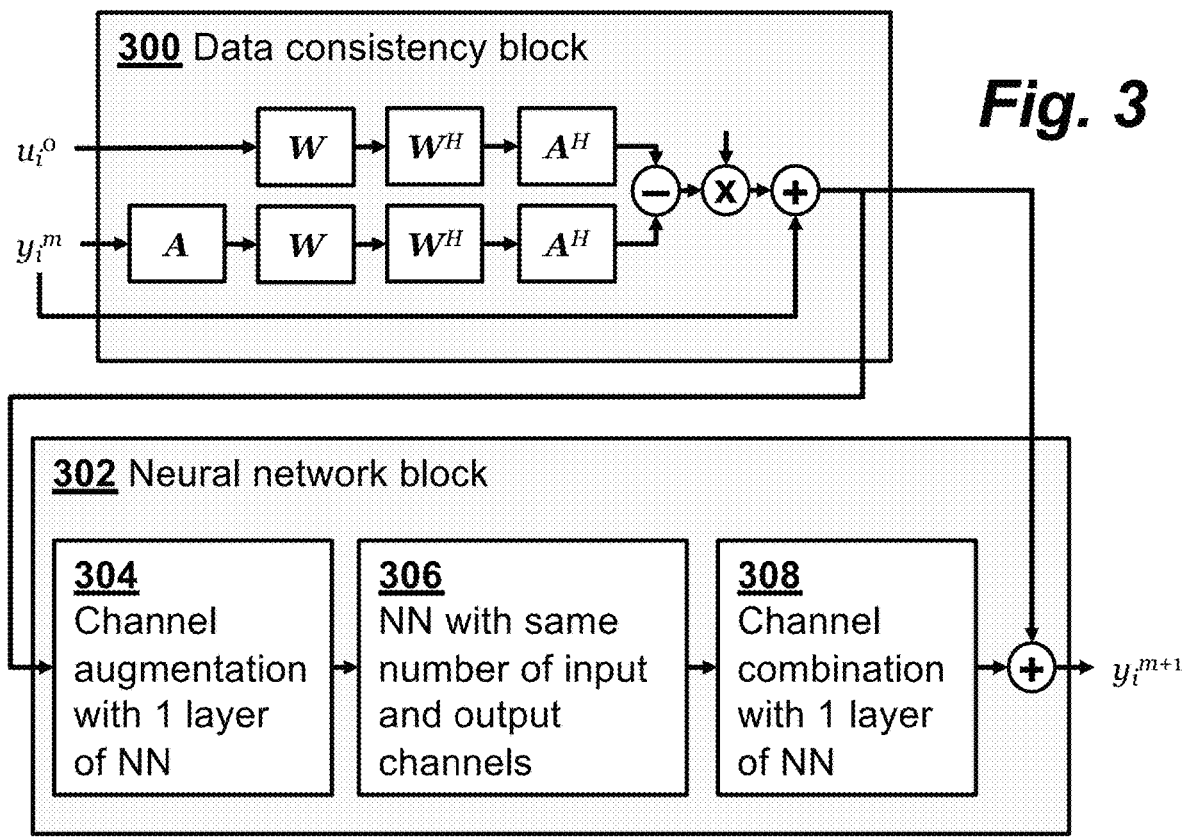
FIG. 3 is a schematic block diagram of a pair of blocks in a neural network architecture used in an MRI apparatus according to an embodiment of the invention.

FIG. 3 shows details of the network architecture of a block pair (e.g., 206, 208, 212, 214 of FIG. 2) according to an embodiment of the invention. The pair contains a data consistency block 300 followed by a neural network block 302. The data-consistency block 300 implements an iterative shrinkage thresholding algorithm, and the convolutional neural network (NN) block is a residual neural network.

The data-consistency block 300 promotes data consistency by performing updates to the under-sampled k-space based on data projection algorithms. An iterative shrinkage thresholding algorithm (ISTA) is implemented in the preferred embodiment. The m-th block pair in chain i uses as inputs the k-space measurement $u_i^O$ of the $i^{th}$ slice and the intermediate output image $y_i^{m-1}$ as inputs. The first neural network block uses as an image input $y_i^O$ zeros or an initial low-quality image reconstructed with an inverse Fourier transform of raw data/signal acquired directly from the MR scanner. In the data consistency block 300, A denotes the encoding operator from image to k-space, which includes coil sensitivity maps when the data is acquired with multiple coil channels, and $A^H$ denotes its Hermitian conjugate. The encoding operator A is basically a Fourier transform of the product between the image and the corresponding coil sensitivity maps, and W denotes an optional window function, which is helpful for soft-gated motion correction. The operator W is monotonically correlated with motion estimation. Large motion will yield a value close to 0 for W, and small motion will give W a value close to 1. Detailed designs may vary (linear, quadratic, etc.). Optionally, W may be assumed to be 1. Besides the preferred updating method, ISTA, other updating methods, such as projection onto convex sets (POCS) algorithm and alternating direction method of multipliers (ADMM) algorithm can also be used in this block.

The neural network block 302 contains a deep neural network, which functions as a regularization of the input. Preferably, a residual neural network (ResNet) is used, which includes a channel augmentation layer 304, several convolution layers with fixed number of features 306, and a channel combination layer 308. Other implementations may use, for example, UNet or GAN.

The loss function (210, FIG. 2) is defined to be a function of the N input k-space measurement slices and the N output images of the neural network block 202. It has the following form:

$$loss = \Sigma_{i=1,N}(\|W(Ay_i^M - u_i^O)\|_2^2 + \Sigma_{j=1,J} \lambda_j R_j(y_i^M))$$

where the index i ranges over all slices in each batch of the training set, where $u_i^O$ is the under-sampled input slice to the i-th chain, $y_i^M$ is the output image from the i-th chain, M is the number of iterations of pairs of blocks in the network, $\|W(Ay_i^M - u_i^O)\|_2^2$ denotes the data consistency term, and $\Sigma_j \lambda_j R_j(y_i^M)$ denotes the sum of regularization terms, which are empirically determined, where j in an index over the number J of regularization terms, where J is preferably 1 or 2 but may be larger. Potential regularization functions include but are not limited to l1 norm of the total variation, l1 norm of the wavelet transform, and nuclear norm of multi-phase acquisitions. The factors $\lambda_j$ denote individual weights of each regularization, which are set globally for all slices. The entire optimization problem can be described as:

$$G_{recon} = \underset{G}{\arg\min} \sum_{i=1,N} \left( \|W(A \cdot G(u_i^0) - u_i^0)\|_2^2 + \sum_{j=1,J} \lambda_j R_j(G(u_i^0)) \right)$$

where G denotes the entire network, which means $y_i^M = G(u_i^O)$, and $G_{recon}$ is the trained network for future reconstruction, which minimizes the loss function of input under-sampled k-space measurements $u_i^O$.

The network is preferably implemented in C/C++ code on CPUs or GPUs provided as standard component of the MRI apparatus.

The invention has been illustrated above with an embodiment that includes a number of specific features that may be changed without departing from the scope of the invention. Many possible variations are envisioned. For example, it is not necessary to implement the invention using an iterative shrinkage thresholding algorithm with residual neural networks. There are several potential variations of this method that may benefit other applications. In particular, algorithms other than ISTA can be used for the data-consistency blocks to promote data consistency, such as POCS, ADMM, etc. Network architectures other than ResNet can be used for neural network blocks, such as U-Net, auto-encoder/decoder, depth-wise convolutions, general adversarial network (GAN), etc.

Also, the regularization terms in the loss function can be customized with transforms that promote a variety of image features. For example, total variation extracts the difference between neighboring pixels in an image. Therefore, if we minimize the total variation of an image, the image will appear to be smooth. If the ideal appearance of the image is smooth, then total variation can be added to the loss function to promote the smoothness of the image (which will appear as some $R_j(y_i^M)$ in $\Sigma_j \lambda_j R_j(y_i^M)$). The relative weights of these regularization terms and the data consistency term may also vary. Potential regularization functions include but are not limited to l1 norm of the total variation of the image, l1 norm of the wavelet transform of the image, and nuclear norm of a set of images.

Updates of the trained model can be implemented by including new datasets in the training set. This may improve the generality of the model and result in a more stable reconstruction performance. In the updating, the weights and bias terms in the convolutions will change based on back-propagations of losses computed with the new datasets. This can be triggered every time a new dataset is acquired.

Acquisition parameters (FOV, matrix size, etc.) and sampling patterns of training datasets are not necessarily the same. As demonstrated in FIG. 4 and FIG. 5, different sampling patterns can be used together for training the network. New under-sampled acquisitions with different sampling patterns can be reconstructed with a single trained model. Additionally, different k-space sampling trajectories can be used.

Compared to conventional parallel imaging and compressed sensing (PICS) reconstruction, embodiments of the present invention have a number of advantages and improvements.

Figure 4:
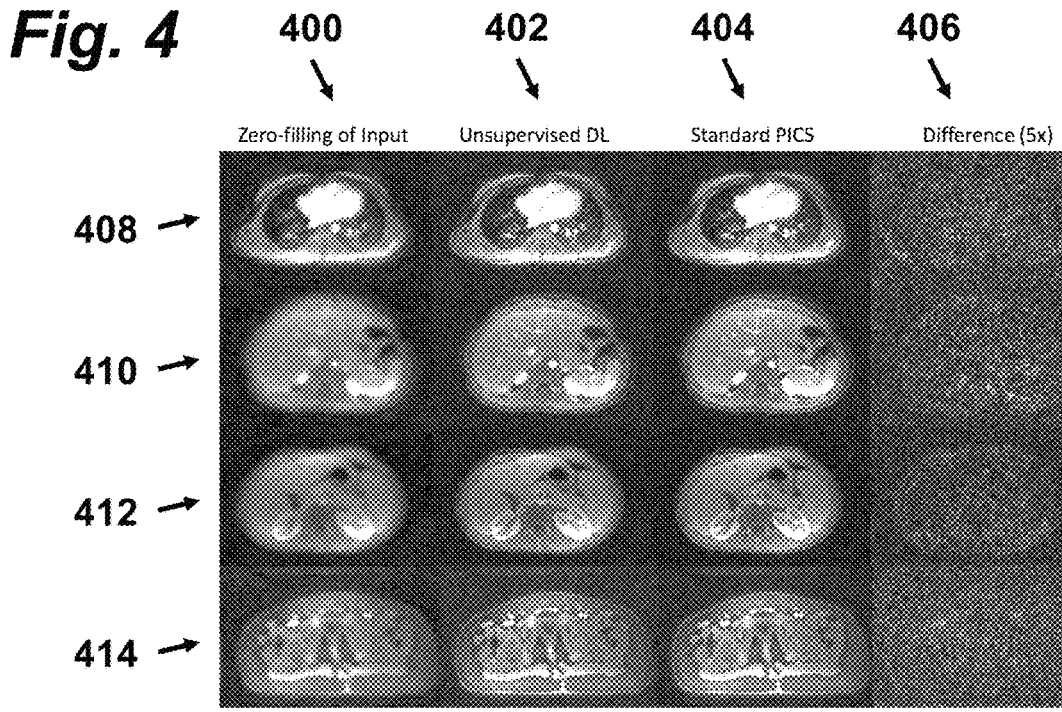
FIG. 4 is an image grid comparing image quality of a standard PICS reconstruction technique with the technique of an embodiment of the present invention.
Figure 5:
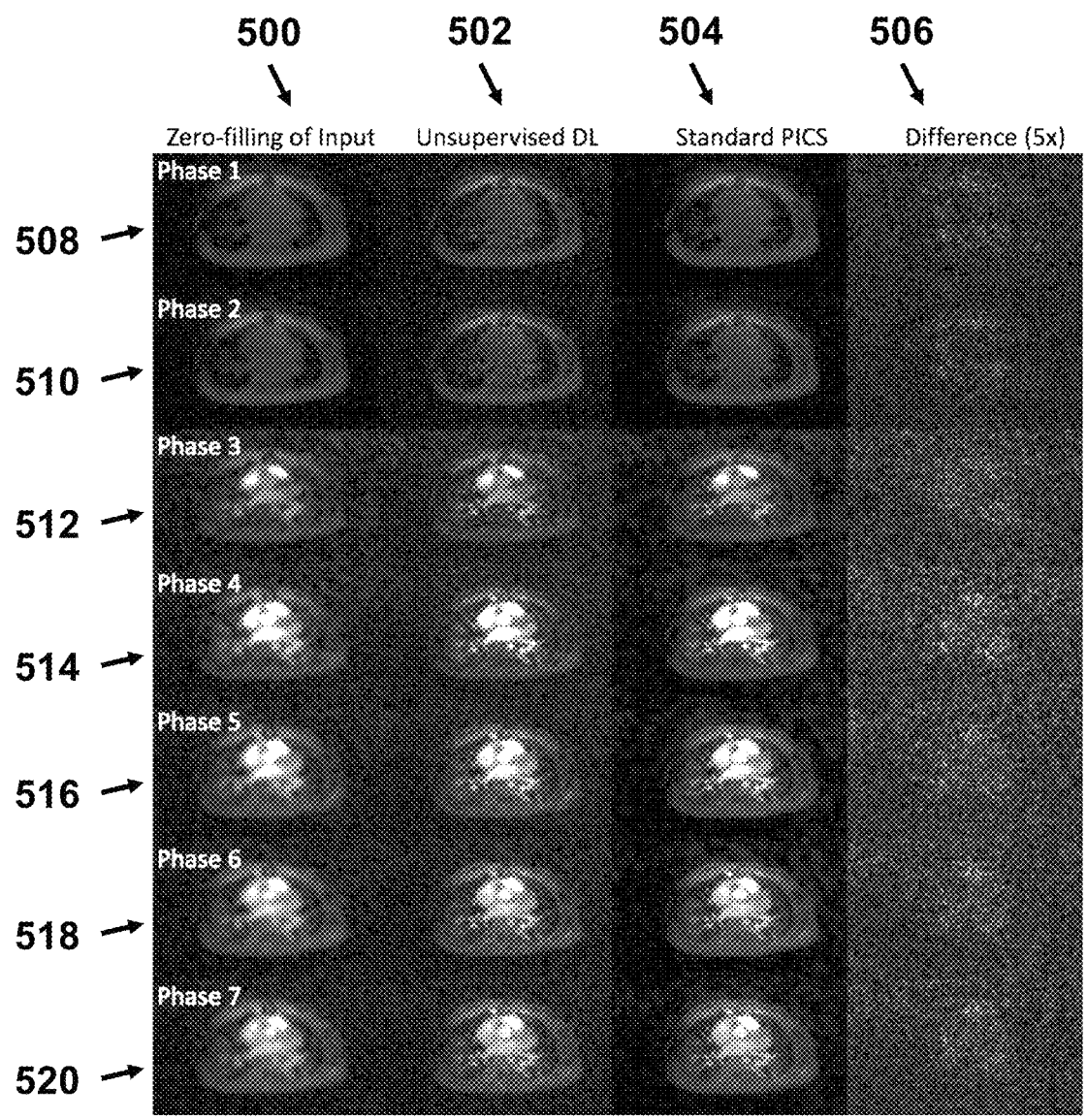
FIG. 5 is an image grid comparing image quality of a standard PICS reconstruction technique with the technique of an embodiment of the present invention

They enable faster reconstruction speed than the conventional PICS reconstruction, with initial results shown in FIG. 4. Columns 400, 402, 404, 406 of the image grid correspond to the zero-filling of input, the unsupervised deep learning reconstructed image, the standard PICS reconstructed image, and the difference between the two reconstructed images (5×), respectively. Rows 408, 410, 412, 414 of the image grid correspond to scans from four different patients. These example results show similar image quality between the proposed unsupervised deep learning (DL) approach and standard PICS reconstruction of single-phase k-space measurements at an under-sampling factor of three. The regularization term is designed to promote sharpness of the image.

When applied clinically, the reconstruction is based on a trained neural network having 4-10 pairs of data-processing and neural-network blocks. In comparison, conventional PICS reconstruction (which processes without neural networks) usually requires more than 30 iterations. The network can be considered as learning optimal step sizes to achieve convergence in a fixed number of steps. This is extremely helpful for high-dimensional acquisitions, such as dynamic contrast-enhanced (DCE) MRI, with initial results shown in FIG. 5, which shows 4D flow imaging, and non-Cartesian MRI. Columns 500, 502, 504, 506 of the image grid correspond to the zero-filling of input, the unsupervised deep learning reconstructed image, the standard PICS reconstructed image, and the difference between the two reconstructed images (5×), respectively. Rows 508, 510, 512, 514, 516, 518, 520 of the image grid correspond to successive points in a time sequence of acquisitions separated by an interval of 3 s. These example results show similar image quality between the unsupervised deep learning (DL) approach and standard PICS reconstruction of multi-phase dynamic contrast-enhanced k-space measurements at an under-sampling factor of about 15. Note all the phases are reconstructed with a single network. The regularization term is designed to promote locally low-rank of the spatial-temporal matrix of each dynamically acquired slice.

Embodiments of the invention avoid the need to tune the regularization coefficient for each type of scan (e.g., scans of different anatomical regions), which is required in PICS reconstruction. This is because the network is trained with a variety of different scans. It only requires constant regularization coefficients, while the regularization coefficients for PICS reconstruction need to be tuned for each type of scan.

The training technique of the present invention is completely unsupervised. This means the training output is not biased by reference images in the training stage. Conventional deep-learning reconstruction methods use reference images as the ground truth. When fully-sampled acquisition is unachievable, additional bias may be introduced in reference images if they are reconstructed from under-sampled k-space with some reconstruction algorithms.

The techniques of the present invention enable the use of flexible loss function design. Loss functions can be customized based on the features of the application. For example, for DCE MRI, locally low-rank can be used in the loss function.

Finally, the techniques of the present invention enable the use of windowing of the raw data, which can be potentially applied in soft-gated motion correction.

The invention claimed is:
1. A method for magnetic resonance imaging comprising:
 a) performing unsupervised training of a deep neural network of an MRI apparatus using a training set of under-sampled MRI scans, wherein each scan comprises slices of under-sampled, unclassified k-space MRI measurements;
 b) performing by the MRI apparatus an under-sampled scan to produce under-sampled k-space data;
 c) updating the deep neural network with the under-sampled scan;
 d) processing the under-sampled k-space data by the updated deep neural network of the MRI apparatus to reconstruct a final MRI image;
 wherein the unsupervised training of the deep neural network of the MRI apparatus using the training set of under-sampled MRI scans comprises:
  i) selecting a set of training batches, where each of the training batches is a set of under-sampled slices randomly selected from the training set of under-sampled MRI scans;
  ii) updating with backpropagation the deep neural network with the training batches by sequentially applying to the deep neural network the training batches, evaluating for each applied training batch an unsupervised loss function.

2. The method of claim 1 wherein the unsupervised loss function is a sum over slices in the applied training batch of a regularization term plus a difference between a slice in the applied training batch and an encoding operator applied to an image output from the deep neural network from applying the slice in the applied training batch.

3. The method of claim 2 wherein the regularization term is a sum over products of constant regularization coefficients and regularization functions of the image output from the deep neural network.

4. The method of claim 2 wherein the deep neural network comprises a set of neural network channels for processing in parallel the slices in the applied training batch, where each of the channels produces the image output from the deep neural network from applying the slice in the applied training batch, where each channel comprises a sequence of block pairs, where each of the block pairs comprises a data consistency block and a neural network block.

5. The method of claim 4 wherein the data consistency block processes the slice of the applied training batch and a prior intermediate image from a prior block pair to produce an output, and the neural network block processes the output to produce an intermediate image for a subsequent block pair, where the neural network block comprises a channel augmentation layer, multiple convolution layers, and a channel combination layer.

6. The method of claim 1 wherein the training set of under-sampled MRI scans comprises scans of more than 100 different subjects, and wherein each scan comprises at least 10 slices of under-sampled, unclassified k-space MRI measurements.

* * * * *